United States Patent
Harding et al.

(10) Patent No.: US 6,744,845 B2
(45) Date of Patent: Jun. 1, 2004

(54) COMPUTED TOMOGRAPHY APPARATUS FOR DETERMINING THE PULSE MOMENTUM TRANSFER SPECTRUM

(75) Inventors: Geoffrey Harding, Hamburg (DE); Jens Peter Schlomka, Hamburg (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 120 days.

(21) Appl. No.: 10/114,766

(22) Filed: Apr. 3, 2002

(65) Prior Publication Data

US 2002/0150202 A1 Oct. 17, 2002

(30) Foreign Application Priority Data

Apr. 3, 2001 (EP) .............................................. 01201215

(51) Int. Cl.[7] .................................................. G21K 1/12
(52) U.S. Cl. ........................................... 378/16; 378/86
(58) Field of Search ............................... 378/4, 16, 19, 378/20, 86–90, 7, 146, 97, 108

(56) References Cited

U.S. PATENT DOCUMENTS

| | | | |
|---|---|---|---|
| 4,745,631 A | * 5/1988 | Paolini | 378/146 |
| 4,995,066 A | 2/1991 | Harding et al. | |
| 4,995,107 A | * 2/1991 | Klingenbeck | 378/7 |
| 5,038,370 A | * 8/1991 | Harding et al. | 378/146 |
| 5,835,555 A | 11/1998 | Barry et al. | |
| 6,125,165 A | * 9/2000 | Warburton et al. | 378/86 |
| 6,470,067 B1 | 10/2002 | Harding | |

FOREIGN PATENT DOCUMENTS

| | | |
|---|---|---|
| EP | 0 074 021 A1 | 8/1982 |
| EP | 0 251 407 A1 | 1/1988 |
| EP | 1 062 914 A1 | 12/2000 |

* cited by examiner

Primary Examiner—Edward J. Glick
Assistant Examiner—Hoon Song
(74) Attorney, Agent, or Firm—Thomas M. Lundin, Esq.

(57) ABSTRACT

The invention relates to a computed tomography apparatus which includes a scanning unit which is rotatable, relative to an examination zone (13), around an axis of rotation (14) which extends through the examination zone (13), and also includes a radiation source (S) for generating a primary fan beam (41) which traverses the examination zone (13), and a two-dimensional detector array (D) which includes a plurality of detector elements and a part of the measuring surface of which detects primary radiation from the primary fan beam (41) whereas an other part of its measuring surface detects scattered radiation produced in the examination zone (13). In order to avoid reconstruction artefacts as much as possible in a computed tomography apparatus of this kind, in accordance with the invention it is proposed to arrange a modulation unit (33) between the radiation source (S) and the examination zone (13) in order to realize a temporally and spatially periodic modulation of the primary fan beam (41).

18 Claims, 3 Drawing Sheets

Figure 1:
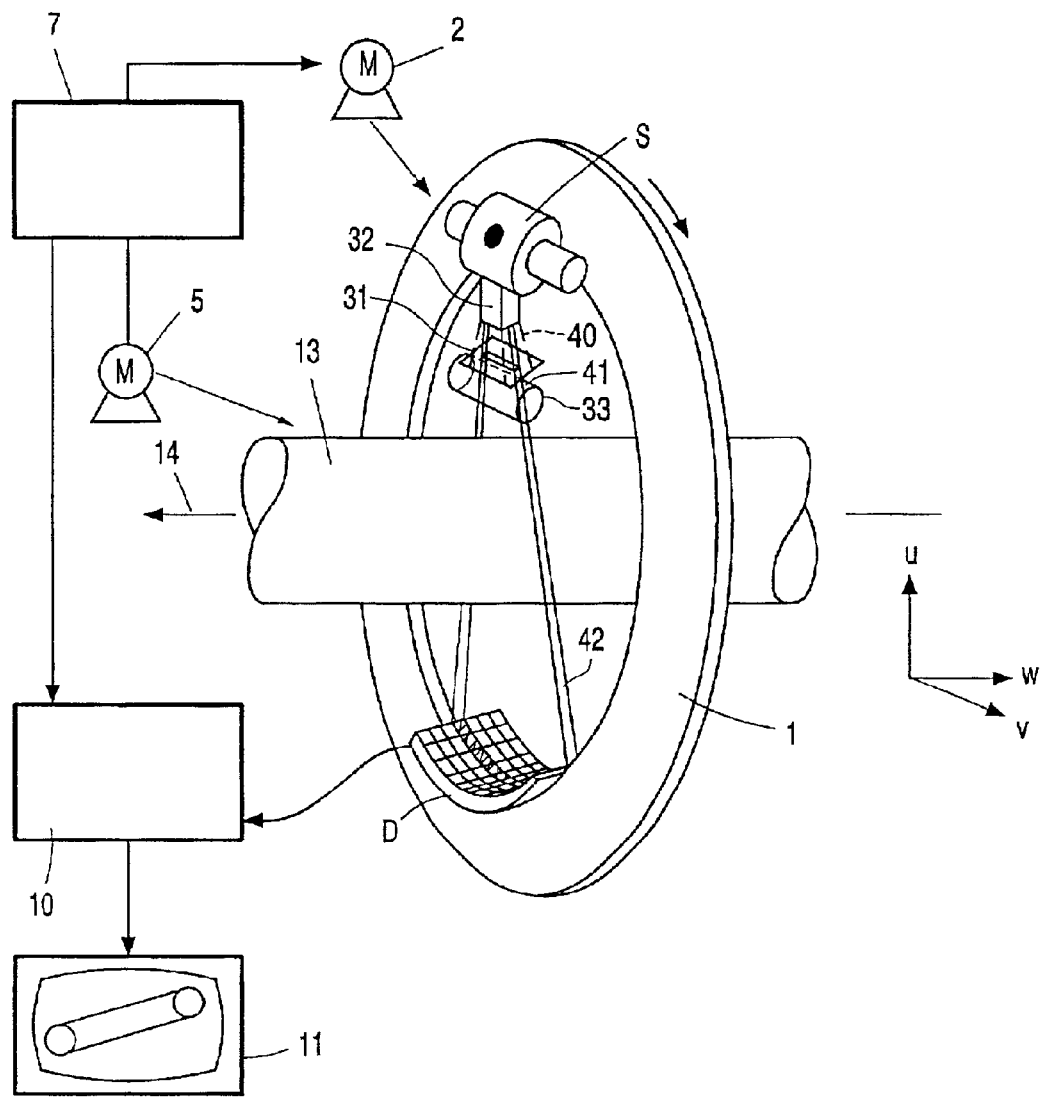

COMPUTED TOMOGRAPHY APPARATUS FOR DETERMINING THE PULSE MOMENTUM TRANSFER SPECTRUM

BACKGROUND

The invention relates to a computed tomography apparatus which includes a scanning unit which is rotatable, relative to an examination zone, around an axis of rotation which extends through the examination zone, and also includes a radiation source for generating a primary radiation fan beam which traverses the examination zone, and a two-dimensional detector array which includes a plurality of detector elements and a part of the measuring surface of which detects primary radiation from the primary radiation fan beam whereas another part of its measuring surface detects scattered radiation produced in the examination zone.

A computed tomography apparatus of this kind is described in European patent application No. 01200652.4. This arrangement detects so-called elastic or coherent scattered X-rays. As is known, such X-rays occur when the X-ray quanta do not loose energy during the scattering process; the type of scattering which involves a loss of energy is referred to as Compton scatter. The elastic scatter is dominant in the case of small scatter angles (for example, angles <10°) whereas the Compton scatter is dominant in the case of large scatter angles. As opposed to Compton scatter, the elastically scattered radiation allows for a characterization of the modular structure of the matter present in the examination zone.

In order to enable detection of coherent scattered radiation by means of the computed tomography apparatus disclosed in the cited European patent application No. 01200652.4, the fan-shaped radiation beam is subdivided into a number of segments which are referred to as pencil beams, so that the detector elements present in a column parallel to the axis of rotation are exposed to primary or scattered radiation from the same segment. Such a subdivision into a number of segments is realized by way of a plurality of lamellas of a collimator device which is arranged between the examination zone and the detector array.

The momentum transfer searched, being proportional to the product of the energy of the scattered X-ray quanta and the sine of half the scatter angle (the scatter angle is the angle enclosed by the path of the scattered X-ray quantum relative to the path that would have been followed by the X-ray quantum in the absence of scattering), can then be reconstructed by means of an iterative algebraic reconstruction technique. For each voxel in the examination zone which is traversed by a primary beam such a reconstruction yields a momentum transfer spectrum (the momentum transfer spectrum represents the intensity of the scattered radiation as a function of the momentum transfer) which is characteristic of the matter in the relevant voxel and hence enables information to be derived as regards the physical composition.

Because the space between the examination zone and the detector array is often very limited, only short lamellas, for example, lamellas having a length of less than 10 cm in the radiation direction, can be used in the described computed tomography apparatus. This leads to segments of the primary fan beam which diverge in the direction of the source, ultimately leading to artefacts in the reconstruction. Therefore, it is an object of the present invention to construct a computed tomography apparatus in such a manner that fan-shaped radiation beam is influenced in such a manner that the coherent scattered radiation incident on the individual detector elements enables unambiguous determination of the momentum transfer and hence a reconstruction which is as free from artefacts as possible.

SUMMARY

This object is achieved in accordance with the invention in that a modulation unit for the temporally and spatially periodic modulation of the primary fan beam is arranged between the radiation source and the examination zone. Because of such modulation of the primary fan beam produced by the radiation source, the coherent scattered radiation from each segment of the primary fan beam can be unambiguously determined by correlation of the measured detector signal with the modulation signal used for the modulation of the radiation. In the section between the radiation source and the examination zone usually enough room is available to accommodate such a modulation unit which requires only a limited amount of space any way. Moreover, unlike the described lamellas of a collimator device, such a modulation unit need not have as large as possible dimensions between the examination zone and the detector array.

Further preferred embodiments are disclosed in the dependent claims.

The primary fan beam can in principle be modulated in different ways. However, the intensity of the primary fan beam is preferably modulated temporally while the phase position of the primary fan beam is modulated spatially as in the embodiment disclosed in claim 2. Furthermore, the modulation is conceived to be such that the transmission factor of the modulation unit, being dependent on the location and the time, exhibits an as large as possible variation, meaning notably that it covers the range from 0 to 1 as well as possible.

A large number of possibilities exist as regards the construction of the modulation unit. Claim 3 discloses a preferred possibility. This embodiment is provided with two diaphragm elements which are diametrically arranged relative to the modulation axis, the modulation axis extending perpendicularly to the axis of rotation and transversely of the direction of propagation of the primary fan beam. These diaphragm elements are arranged helically around the modulation axis and are capable of rotating about this axis so as to achieve the desired modulation by such rotation. In this helical arrangement, the diaphragm elements are led once through 180° around the modulation axis; however, they may also be led an integer multiple of 180° around the modulation axis.

Various implementations of the embodiment of the computed tomography apparatus as disclosed in claim 3, notably of the diaphragm elements, are given in the claims 4 to 6.

As is indicated in claim 7, the modulation unit may also be configured in such a manner that there is formed a plurality of radiation beam units with each time a separate modulation.

Modulation is realized in the simplest way by selecting a sinusoidal modulation function, meaning that the transmission factor of the modulation unit, being dependent on the location and the time, varies sinusoidally in dependence on the location and the time.

DRAWINGS

The invention will be described in detail hereinafter with reference to the drawings.

Figure 2:
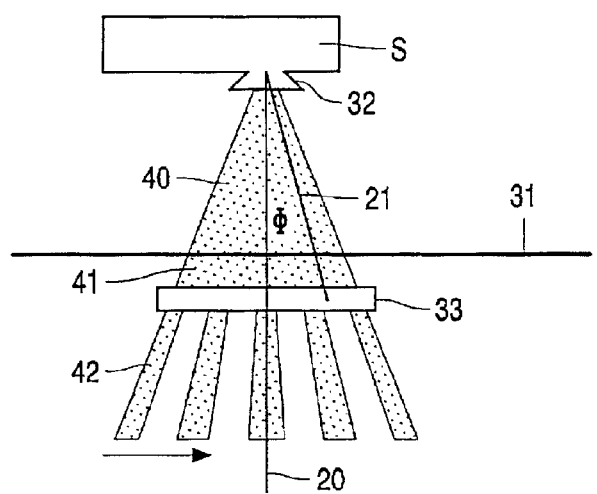
Figure 2:
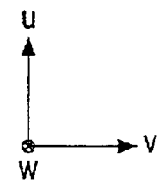
Figure 3:
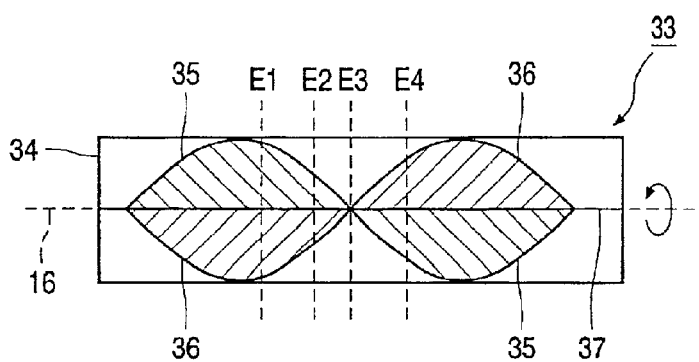
Figure 3:
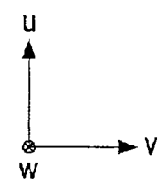
Figure 4:
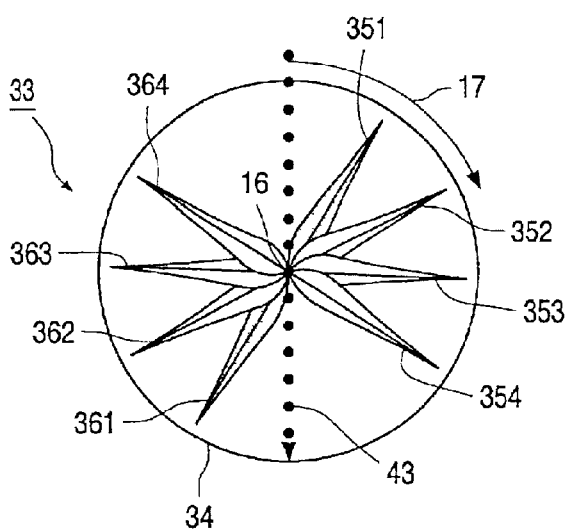
Figure 4:
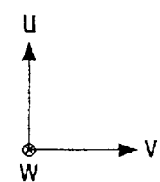
Figure 5:
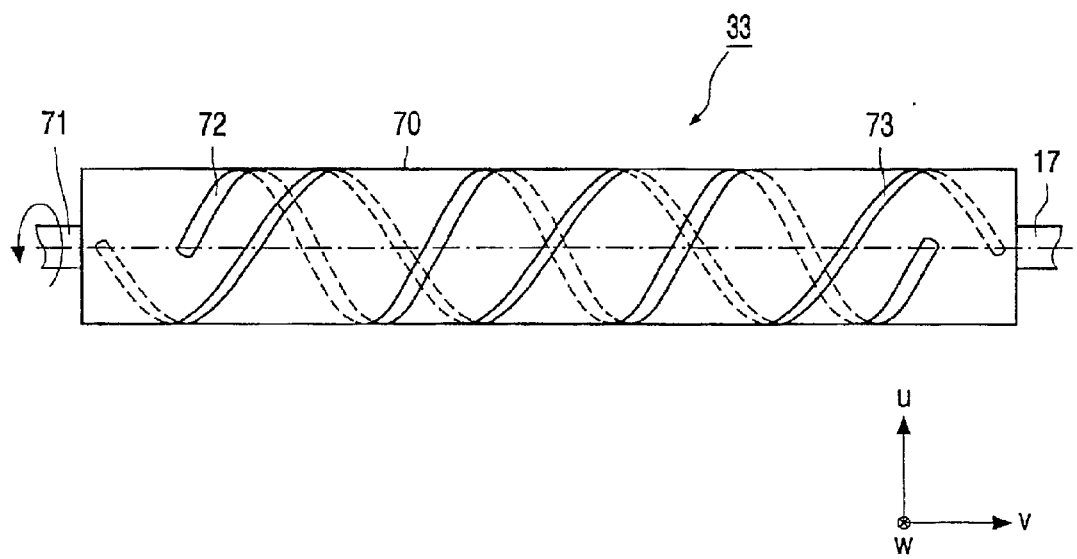
Figure 6:
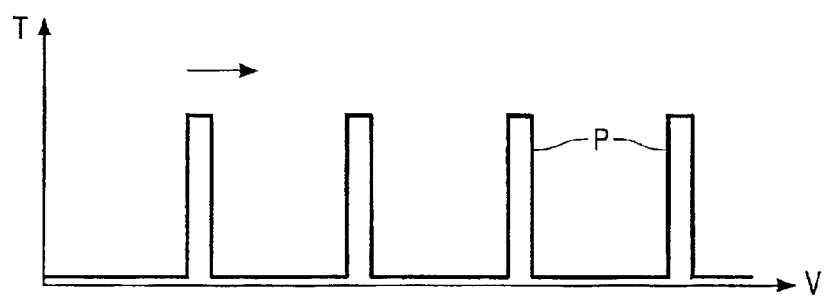

FIG. 1 is a diagrammatic representation of a computed tomography apparatus in accordance with the invention, FIG. 2 shows a part of the computed tomography apparatus in accordance with the invention as shown in FIG. 1, FIG. 3 shows a first embodiment of a modulation unit in accordance with the invention, FIG. 4 is a cross-sectional view of a modulation unit as shown in FIG. 3, FIG. 5 shows a second embodiment of a modulation unit in accordance with the invention, and FIG. 6 shows a variation of the transmission factor in the modulation unit shown in FIG. 5.

DESCRIPTION

The computed tomography apparatus shown in FIG. 1 includes a gantry 1 which is capable of rotation about an axis of rotation 14; to this end, the gantry 1 is driven by a motor 2. A radiation source S, for example, an X-ray source, is mounted on the gantry 1. Using a first diaphragm device 32, first a conical radiation beam 40 is generated, said beam being incident on a second diaphragm arrangement 31, being a so-called slit diaphragm, which forms a fan-shaped radiation beam 41, that is, a so-called primary fan beam, therefrom. The primary fan beam 41 extends perpendicularly to the axis of rotation 14 and, because of the small slit width, it has only small dimensions in the direction of the axis of rotation 14 (for example, 1 mm). The primary fan beam 41 is then incident on a modulation unit 33 which temporally and spatially modulates the radiation, thus yielding a modulated primary fan beam 42.

The modulated primary fan beam 42 penetrates a cylindrical examination zone 13 in which, for example, a patient on a patient table (both not shown) or a technical object may be present so as to be examined. After having traversed the examination zone 13, the fan beam 42 is incident on a two-dimensional detector array D which is mounted on the gantry 1 and includes a plurality of detector elements which are arranged in the form of a matrix. The detector elements are arranged in rows and columns, the columns extending parallel to the axis of rotation 14 while the rows extend in planes perpendicular to the axis of rotation 14, for example, along an arc of a circle around the radiation source S. Generally speaking, the detector rows comprise significantly more detector elements (for example, 1000) than the detector columns (for example, 16). The primary fan beam 42 is oriented in such a manner that it is incident on the central detector row of the detector array D which is denoted by shading in FIG. 1.

A linear movement of the examination zone 13 along the axis of rotation 14 under the influence of the motor 5 can be superposed on the rotary movement of the gantry 1, resulting in a helical scanning motion of the radiation source S and the detector array D. When a technical object is to be examined, the gantry 1 may also be stationary and the object may be rotated around the axis of rotation 14.

The measuring data acquired by the detector array D is applied to an image processing computer 10 which reconstructs the desired images or evaluates the measuring data in another manner. The reconstructed images or other data determined can be displayed on a display screen 11. The image processing computer 10 is controlled by a control unit 7, like the motors 2 and 5.

FIG. 2 shows a detail of the computed tomography apparatus shown in FIG. 1. Starting from the X-ray source S, the first diaphragm 32 forms a conical X-ray beam 40 which is subsequently incident on the slit diaphragm 31. From this diaphragm primary radiation 41 emerges in the form of a fan beam which is also incident on the modulation unit 33 so that the desired modulated primary fan beam 42 is generated; this beam is subsequently incident on the examination zone which is not shown herein.

The slit of the slit diaphragm 31 has a small dimension of, for example, only 1 mm in the w direction. The slit, however, is significantly wider in the v direction. This dimension can also be characterized by an angle $\Phi$ which characterizes the angle between the direct connecting line 20 between the focal point of the X-ray source S and the center of the detector D or the center of rotation of the computed tomography apparatus and a primary beam 21 of the primary radiation beam 41. The angle variable $\Phi$ satisfies the condition $-\Phi_{fan/2} \leq \Phi \leq \Phi_{fan/2}$, where $\Phi_{fan/2}$ corresponds to half the angle of the primary fan beam 41. The modulation unit 33 is configured in such a manner that its transmission factor $T(\Phi t)$ varies periodically as a function of the angle $\Phi$ and with the time t, be it that the condition $0 \leq T(\Phi, t) \leq 1$ is always satisfied. The primary fan beam 41 is thus spatially and temporally modulated; this offers special advantages for the evaluation of the scattered radiation measured by the detector array D as will be described in detail hereinafter.

For example, the transmission factor T of the modulation unit 33 may be chosen in conformity with the following rule:

$$T(\Phi, t) = A_0 \sin(A_1 \cdot \Phi + A_2 \cdot t).$$

As can be clearly seen from this rule, in the case of a fixed angle $\Phi$ the transmission varies periodically as a function of time at a frequency $A_2/(2\pi)$. The phase of this transmission rule is repeated even at points of the v axis along the slit of the slit diaphragm 31, that is, each time after an interval $\Delta\Phi = 2\pi/A_1$. The variable $A_1$ should, therefore, have values of $2\pi n/\Phi_{fan}$, where n represents a positive integer value. The significance of the choice of the parameter n will be explained in detail hereinafter.

The FIGS. 3 and 4 show a feasible embodiment of the modulation unit 33 which satisfies the above conditions. FIG. 3 is a side elevation of such a modulation unit 33 from the same perspective as FIG. 2. In a radiation transparent housing 34 there is shown a shaft 37 which extends along a modulation axis 16 extending in the v direction. On the shaft 37 two diaphragm elements 35, 36 are arranged so as to be diametrically oppositely situated, said elements extending helically around the shaft 37 in the v direction. These diaphragm elements 35, 36 may be compared, for example, with two threads of a screw which are arranged so as to be rotated 180° relative to one another while commencing from the same point along the v axis.

FIG. 4 shows cross-sections of the modulation unit 33 along the planes E1, E2, E3, E4 shown in FIG. 3, that is, planes extending perpendicularly to the v axis. The primary beam 43 is represented by a dotted line therein and extends through the modulation axis 16. Inside the housing 34 the diaphragm elements 35, 36 are shown in a cross-sectional view, the Figure showing different cross-sections in an adjacent fashion. The shaded position of the diaphragm elements 351, 361 represents the cross-section of the diaphragm elements 35, 36 in the plane E1. The further positions 352, 353, 354 and 362, 363, 364 represent the respective cross-section of the diaphragm elements 35, 36 in the planes E2, E3, E4. Thus, a linear relationship exists between the illustrated cross-sections of the diaphragm elements 35, 36 and the angle $\Phi$ as shown in FIG. 2; this means that, in dependence on the angle $\Phi$ considered, the diaphragm elements 35, 36 occupy a different angular position in a cross-sectional view as shown in FIG. 4.

The diaphragm elements 35, 36 are preferably made of a material such as aluminium. Using a motor (not shown), the diaphragm elements 35, 36 or the shaft 37 can be driven in such a manner that the diaphragm elements 35, 36 rotate around the modulation axis 16 with a known phase and a constant angular speed in such a manner that the primary radiation is temporally encoded at a fixed angle Φ, the phase of the modulation being known and linearly proportional to the angle Φ. It is to be noted that the embodiment of the modulation unit 33 shown could be compared with the cutting device of a hand-operated lawn mower provided with two diametrically arranged cutting blades extending helically around the axis of rotation of the cutting device.

The thickness of the diaphragm elements 35, 36 is chosen to be such that a sinusoidal transmission is obtained when they are rotated. For example, for the variable $A_0$ of the above transmission rule the value 0.495 could be chosen and the value 0.505 for the variable $A_2$. The modulation unit shown in the FIGS. 3 and 4 realizes a temporal modulation of the intensity of the primary radiation 41 where the phase of the modulation is linked to the position along the fan beam 41.

The gantry 1 rotates for the acquisition of measuring values, so that the detector elements of the detector array D detect the primary radiation and the scattered radiation from a plurality of angular positions. The detector element or elements at the center of each detector column detects (detect) the primary radiation whereas the scattered radiation (secondary radiation) is detected by the detector elements which are situated further outwards in each column. The momentum transfer, whose spectrum is to be reconstructed as a function of the location u, v, is known to be the product of the energy of the scattered X-ray quanta and the sine of half the scatter angle. In order to enable the momentum transfer to be determined, on the one hand the scatter angle must be known and on the other hand the energy of the scattered X-ray quantum. The scatter angle is given by the position of the detector element and the position of the point in the primary fan beam in which the scatter process has taken place. The energy of the scattered X-ray quanta must either be measured, implying that the detector elements should be capable of energy-resolved measurement, or use must be made of X-rays with quantum energies from an as small as possible range (monochromatic X-rays in the ideal case).

In order to reconstruct the location-dependent momentum transfer spectrum, it is first necessary to carry out a phase-sensitive detection as described, for example, in D. C. Champeney "Fourier transforms and their physical applications", Academic Press, 1973, for the scattered signal arriving at the detector. To this end, a cross-correlation is performed between the scatter signal detected by a given detector element, that is, the scattered radiation measured by a given detector element, and the sinusoidal modulation signal generated by the modulation unit for the corresponding segment of the primary fan beam. This segment of the primary fan beam is situated in a plane which is determined by the focus of the X-ray source and the detector column in which the relevant detector element is situated. Because the scatter signal is always in phase with the primary beam wherefrom the associated scatter has originated by scattering on an object, the cross-correlation always produces a positive result, whereas a cross-correlation of two signals which are not in phase tends towards zero.

The coherent scatter of a pencil-shaped beam has the highest intensity value in the case of a small scatter angle and tends towards zero as the scatter angle increases. When a given detector element is considered, therefore, the contributions of scatter from segments of the primary fan beam decrease when the scatter angle of scatter incident on the relevant detector element increases. For scatter angles larger than 10°, therefore, no coherent scatter can reach a detector element from neighboring segments of the primary fan beam. Therefore, the primary fan beam can be subdivided into a given number of, for example, five sections (as shown in FIG. 2), each section having an identical phase characteristic. In this case the above parameter $A_1$ of the transmission rule would have the value $2\pi n/\Phi_{fan}$, where n=5.

In addition to the described possibilities for modulation, other possibilities are feasible. It is to be ensured merely that the temporal modulation regularly varies at each fixed point of the primary fan beam and that the phase of the temporal modulation varies continuously along the primary fan beam.

FIG. 5 shows a further embodiment of a modulation unit 33. The modulation unit therein has a housing 70 which is made of a material having a thickness such that the incident X-rays are practically completely absorbed. One of the hollow shafts 71 is connected to a motor in order to enable rotation of the modulation unit 33 around the modulation axis 16. In the housing there are provided two helical slits 72, 73 which are mutually offset, extend around the axis of modulation 16 and allow passage of the X-rays. The inclinations of the slits 72, 73, the number of turns, their axial length and width as well as their relative positions are adapted to the desired modulation and are shown merely by way of example herein. Such a modulation unit is also capable of achieving the desired modulation of the primary fan beam. The primary fan beam is thus decomposed into a kind of "comb" function as shown in FIG. 6 where the "teeth" P of the "comb" extend along the axis v in a regularly recurrent fashion.

It is also to be noted that one or more lamellas of a collimator array as described in the European patent application 01200652.4 may also be provided between the object to be examined and the detector array.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A computed tomography apparatus comprising:

a scanning unit which is rotatable, relative to an examination zone, around an axis of rotation which extends through the examination zone;

a radiation source for generating a primary radiation fan beam which traverses the examination zone;

a two-dimensional detector array which includes a plurality of detector elements defining a measuring surface, a first part of the measuring surface for detecting primary radiation from the primary fan beam and a second part of the measuring surface for detecting scattered radiation produced in the examination zone;

a modulation unit for the temporally and spatially periodic modulation of the primary fan beam, said modulation unit disposed between the radiation source and the examination zone and, a determining unit for determining a momentum transfer spectrum from cross-correlations between the measured scattered radiation of the individual detector elements and a modulation signal used for the modulation of the primary fan beam.

2. A computed tomography apparatus as claimed in claim 1, wherein the modulation unit is constructed such that the intensity of the modulated primary fan beam has an intensity that is temporally modulated and a phase position that is spatially modulated.

3. A computed tomography apparatus as claimed in claim 1, wherein the modulation unit is cylindrically symmetrically arranged around a modulation axis which extends perpendicularly to the axis of rotation and the connecting line between the focal point of the radiation source and the center of the detector array, and comprises two diaphragm elements which are diametrically arranged relative to the modulation axis, are arranged helically around the modulation axis, and are rotatable about the modulation axis.

4. A computed tomography apparatus as claimed in claim 3, wherein the diaphragm elements are rotatable at a constant angular speed around the modulation axis for the temporal and spatial modulation of the primary fan beam.

5. A computed tomography apparatus as claimed in claim 3, wherein the diaphragm elements comprise diaphragm blades which are radiation attenuating and are mounted so as to be helical and 180° offset on a shaft extending along the modulation axis.

6. A computed tomography apparatus as claimed in claim 3, wherein the modulation unit comprises a radiation attenuating external wall and the diaphragm elements include two radiation transparent slits which extend helically and in an offset fashion in the external wall.

7. A computed tomography apparatus as claimed in claim 1, wherein in order to subdivide the primary fan beam, the modulation unit is subdivided into a plurality of neighboring fan beam units and is arranged for the separate modulation of the fan beam units.

8. A computed tomography apparatus as claimed in claim 1, wherein the modulation unit comprises means for sinusoidal temporal and spatial modulation of the primary fan beam.

9. A computed tomography apparatus comprising:
a scanning unit which is rotatable, relative to an examination zone, around a scanner axis of rotation which extends through the examination zone;
a radiation source for generating a radiation beam directed towards the examination zone;
a detector disposed across the examination zone from the radiation source, said detector including a plurality of detector elements for detecting primary radiation and scattered radiation that passes through the examination zone;
a modulation unit disposed between the radiation source and the examination zone for temporally and spatially modulating the radiation beam; and
cross-correlation means for cross-correlating the spattered radiation with a modulation signal used for the modulation of the radiation beam whereby a location-dependent momentum transfer spectrum is reconstructed.

10. A computed tomography apparatus as claimed in claim 9, wherein the modulation unit comprises temporal means for temporally modulating the intensity of the modulated radiation beam and spatial means for spatially modulating the phase position of the modulated radiation beam.

11. A computed tomography apparatus as claimed in claim 9, wherein the modulation unit is cylindrically symmetrically arranged around a modulation axis which extends perpendicularly to the scanner axis of rotation and a line passing from the focal point of the radiation source and the center of the detector array, and comprises a plurality of diaphragm elements arranged helically around the modulation axis.

12. A computed tomography apparatus as claimed in claim 11, wherein the diaphragm elements rotate at a constant angular speed around the modulation axis.

13. A computed tomography apparatus as claimed in claim 11, wherein the diaphragm elements comprise diaphragm blades which are radiation attenuating and are mounted so as to be helical and 180° offset from one another on a shaft extending along the modulation axis.

14. A computed tomography apparatus as claimed in claim 11, wherein the modulation unit comprises a radiation attenuating external wall and the diaphragm elements include radiation transparent slits which extend helically and in an offset fashion from one another in the external wall.

15. A computed tomography apparatus as claimed in claim 9, wherein the modulation unit comprises dividing means for dividing the radiation beam into a plurality of radiation beam units.

16. A computed tomography apparatus as claimed in claim 9, wherein the modulation unit comprises sinusoidal means for sinusoidally modulating the radiation beam temporally and spatially.

17. A method of computed tomography comprising the steps of:
projecting a fan-shaped beam of radiation from a radiation source towards an examination region;
modulating the fan-shaped beam of radiation temporally and spatially 7 using a modulation unit disposed between the radiation source and the examination region;
detecting primary radiation and scattered radiation using a radiation detector array after the primary and scattered radiation have passed through the examination region; and
obtaining a momentum transfer spectrum of the scattered radiation.

18. A method of computed tomography according to claim 17 wherein the step of modulating the fan-shaped beam of radiation includes sinusoidally modulating the fan-shaped beam of radiation.

* * * * *